United States Patent
LaRose et al.

(10) Patent No.: US 8,152,493 B2
(45) Date of Patent: Apr. 10, 2012

(54) CENTRIFUGAL ROTARY BLOOD PUMP WITH IMPELLER HAVING A HYDRODYNAMIC THRUST BEARING SURFACE

(75) Inventors: Jeffrey A. LaRose, Parkland, FL (US); Charles R. Shambaugh, Jr., Coral Gables, FL (US); Daniel G. White, Pembroke Pines, FL (US); Lisandro Rivera, Miramar, FL (US); Kartikeyan Trichi, Miami Lakes, FL (US); Palanivelu Thyagarajan, legal representative, San Jose, CA (US)

(73) Assignee: Hearthware Inc., Miami Lakes, FL (US)

( * ) Notice: Subject to any disclaimer, the term of this patent is extended or adjusted under 35 U.S.C. 154(b) by 578 days.

(21) Appl. No.: 12/150,662

(22) Filed: Apr. 30, 2008

(65) Prior Publication Data

US 2009/0234447 A1 Sep. 17, 2009

Related U.S. Application Data

(60) Provisional application No. 60/926,885, filed on Apr. 30, 2007.

(51) Int. Cl.
*F04B 17/00* (2006.01)
*A61M 1/10* (2006.01)
*F01D 3/00* (2006.01)

(52) U.S. Cl. ........ 417/420; 623/3.13; 415/104; 415/900; 417/423.12

(58) Field of Classification Search ............. 417/423.12, 417/420, 355, 356, 423.7; 600/16; 623/3.13, 623/3.14, 3.1, 3.15, 3.23, 3.24, 3.25; 415/104, 415/900

See application file for complete search history.

(56) References Cited

U.S. PATENT DOCUMENTS

| | | | |
|---|---|---|---|
| 5,049,134 A | 9/1991 | Golding et al. | |
| 5,055,005 A | 10/1991 | Kletschka | |
| 5,112,202 A | 5/1992 | Oshima et al. | |
| 5,158,440 A | 10/1992 | Cooper et al. | |
| 5,195,877 A | 3/1993 | Kletschka | |
| 5,324,177 A | 6/1994 | Golding et al. | |
| 5,370,509 A | 12/1994 | Golding et al. | |
| 5,470,208 A | 11/1995 | Kletschka | |
| 5,746,575 A | 5/1998 | Westphal et al. | |
| 5,769,069 A * | 6/1998 | Caffell ........................... | 126/634 |
| 5,863,179 A | 1/1999 | Westphal et al. | |
| 6,030,188 A * | 2/2000 | Nojiri et al. ................... | 417/420 |
| 6,071,093 A * | 6/2000 | Hart ............................ | 417/424.2 |

(Continued)

OTHER PUBLICATIONS

International Search Report issued by the International Searching Authority (ISA/US) in connection with International Application No. PCT/US2008/005520.

(Continued)

*Primary Examiner* — Devon C Kramer
*Assistant Examiner* — Nathan Zollinger
(74) *Attorney, Agent, or Firm* — John P. White; Cooper & Dunham LLP

(57) ABSTRACT

A rotary blood pump may include one or more motor stators overlying exterior surfaces of a wall defining a pumping chamber. A rotatable impeller within the pumping chamber may have a hydrodynamic thrust bearing surface adapted to constrain a position of the impeller along an axis of rotation relative to the wall when the impeller is rotating about the axis of rotation. The impeller position may then be constrained without requiring a constant polarity magnetic force to be applied in the axial direction from a fixed position of the housing.

25 Claims, 20 Drawing Sheets

U.S. PATENT DOCUMENTS

| | | | |
|---|---|---|---|
| 6,074,180 A | 6/2000 | Khanwilkar et al. | |
| 6,155,969 A | 12/2000 | Schima et al. | |
| 6,183,220 B1 | 2/2001 | Ohara et al. | |
| 6,234,772 B1 * | 5/2001 | Wampler et al. | 417/423.12 |
| 6,439,845 B1 | 8/2002 | Veres | |
| 6,623,475 B1 * | 9/2003 | Siess | 604/891.1 |
| 6,641,378 B2 | 11/2003 | Davis et al. | |
| 6,846,168 B2 | 1/2005 | Davis et al. | |
| 6,966,748 B2 * | 11/2005 | Woodard et al. | 415/104 |
| D514,125 S * | 1/2006 | Cook | D15/7 |
| 7,416,525 B2 * | 8/2008 | Wampler et al. | 600/16 |
| 7,682,301 B2 * | 3/2010 | Wampler et al. | 600/16 |
| 2004/0143151 A1 | 7/2004 | Mori et al. | |
| 2005/0084398 A1 | 4/2005 | Wampler et al. | |
| 2005/0095151 A1 * | 5/2005 | Wampler et al. | 417/423.12 |
| 2005/0135948 A1 | 6/2005 | Olsen et al. | |
| 2006/0030748 A1 * | 2/2006 | Woodard et al. | 600/16 |
| 2006/0083642 A1 * | 4/2006 | Cook | 417/423.1 |
| 2006/0245959 A1 | 11/2006 | LaRose et al. | |
| 2007/0078293 A1 * | 4/2007 | Shambaugh et al. | 600/16 |

OTHER PUBLICATIONS

International Preliminary Report on Patentability issued by the International Bureau of WIPO on Nov. 3, 2009 in connection with International Application No. PCT/US2008/005520.

Written Opinion of the International Searching Authority issued by the International Searching Authority (ISA/US) in connection with International Application No. PCT/US2008/005520.

* cited by examiner

ND RY BLOOD PUMP
WITH IMPELLER HAVING A
HYDRODYNAMIC THRUST BEARING
SURFACE

This application claims benefit from U.S. Provisional Application No. 60/926,855, filed Apr. 30, 2007, the content of which is hereby incorporated herein by reference into this application.

CROSS-REFERENCE TO RELATED APPLICATION

The present application claims benefit of the filing date of U.S. Provisional Patent Application No. 60/926,885 filed Apr. 30, 2007, the disclosure of which is hereby incorporated by reference herein.

FIELD OF THE INVENTION

The present invention relates to rotary pumps and, more specifically, to centrifugal rotary blood pumps and methods of therapeutic support utilizing such pumps, in which a submerged impeller within the pump rotates on wearless hydrodynamic and magnetic bearings to pressure blood to move from a pump inlet to a pump outlet.

BACKGROUND OF THE INVENTION

Clinical applications of ventricular assist devices to support patients with end-stage heart disease, as a bridge to cardiac transplantation, or as an end stage therapeutic modality have become an accepted clinical practice in cardiovascular medicine. It is estimated that greater than 35,000 persons suffering from end stage cardiac failure are candidates for cardiac support therapy.

Ventricular assist devices may utilize a blood pump for imparting momentum to a patient's blood thereby driving the blood to a higher pressure. One example of a ventricular assist device is a Left Ventricular Assist Device (LVAD). The LVAD is inserted into the left ventricle of the patient's heart where oxygenated blood enters the LVAD through a blood inlet of the LVAD. The LVAD then imparts momentum to the blood. By connecting a blood outlet of the LVAD to the patient's aorta, pumped blood may reenter the patient's circulatory system.

Ventricular assist devices, such as the LVAD, have heretofore utilized mechanical positive displacement pumps and rotary pumps. Positive displacement pumps draw blood into a chamber by increasing the volume of the chamber. Such mechanical pumps are normally large and prone to mechanical wear. The human heart is a natural example of a positive displacement pump. A rotary pump forces blood by the spinning of an impeller within the pump. In general, the impeller of a rotary pump imparts momentum to the blood through the use of impeller blades or vanes which push the blood.

Rotary blood pumps may be either centrifugal or axial. In a typical centrifugal blood pump, blood enters the pump along the axis of rotation of the impeller and exits the pump tangentially. In a typical axial blood pump, blood enters the pump along its axis of rotation and exits the pump along the axis of rotation.

Traditionally, rotary blood pumps include a rotor consisting of a shaft and an impeller coupled to the shaft. Mechanical bearings are used to stabilize the rotor, both axially and radially, so the impeller could remain free to rotate smoothly while being constrained in the axial and radial directions. Mechanical bearings within the volume of blood have become a source of thrombosis. Moreover, as the use of mechanical bearings necessitated the protrusion of the shaft beyond the pumping chamber, a seal was required to prevent the escape of blood from the pumping chamber. This too became a source of thrombosis and sometimes hemolysis, as well as premature wear.

To minimize the risk of thrombosis and failed seals, sealless rotary blood pumps have been developed. For example, U.S. Pat. No. 5,695,471 to Wampler relates to a sealless rotary blood pump in which the rotor or impeller can be suspended within the pumping chamber by the use of magnetic or fluid forces.

Magnetic or fluid forces used to suspend the impeller within the pumping chamber could serve to stabilize the impeller, allowing for rotation while preventing excessive axial or radial movement. Wearless stabilization of an impeller can be achieved by magnetic bearings and hydrodynamic bearings.

Several forms of magnetic bearings have been developed. In one form, passive magnetic bearings in the form of permanent magnets can be embedded in both the rotor and the pump housing to provide magnetic coupling that may keep the impeller suspended in position within the pump casing.

Active magnetic bearings in the form of electromagnets can be used, for example, in or on the pump housing, magnetically to couple with and to drive the impeller. Power to the electromagnets may then be varied, as required, to adjust the magnetic field in response to displacement so that the impeller may be kept in position.

Because of the complexity of active magnetic bearings, rotary blood pumps have been developed that use passive magnetic bearings and hydrodynamic bearings to provide axial and radial constraint of the impeller in the pumping chamber. For example, U.S. Pat. No. 6,234,772, to Wampler et al. (the '772 patent), provides radial restoring forces and hydrodynamic bearings to constrain axial motion.

There remains a need for smaller and more efficient rotary blood pumps. In particular, there remains a need for wearless centrifugal pumps with hydrodynamic bearings and improved continuous fluid flow paths within the pump to further diminish the risks of hemolysis and thrombosis in the blood being pumped. By developing more sophisticated rotary blood pump impellers with hydrodynamic bearings and passive magnetic bearings, the physical size, performance and efficiency of the rotary blood pump may be improved to the point where consistent and reliable therapeutic support may be provided.

SUMMARY OF THE INVENTION

A rotary blood pump may include one or more motor stators overlying exterior surfaces of a wall defining a pumping chamber. A rotatable impeller within the pumping chamber may have a hydrodynamic thrust bearing surface adapted to constrain a position of the impeller along an axis of rotation relative to the wall when the impeller is rotating about the axis of rotation. By the rotation of the impeller and the action of the thrust bearing surface, the impeller position may be constrained without requiring a constant polarity magnetic force to be applied in the direction of the rotational axis from a fixed position of the housing.

In accordance with one aspect of the invention, a rotary blood pump is provided which includes a housing having a pumping chamber defined by a wall. One or more electromagnetic motor stators overlie one or more exterior surfaces of the wall. A rotatable impeller within the pumping chamber may have a plurality of spaced apart impeller bodies. In a particular embodiment, each of the impeller bodies may have a pair of straight side walls of unequal length and the side walls of each impeller body may extend from an inner edge to respective peripheral edges of the impeller body. Such inner edges may be forward of the peripheral edges in the direction of rotation of the impeller.

In one embodiment, a centrifugal rotary blood pump for implantation within the pericardial space includes a housing defining a pumping chamber. The pumping chamber may have an axial blood inlet and a tangential volute defining a blood outlet. One or more magnetic motor stators can be provided outside of the pumping chamber. A rotatable impeller within the pumping chamber is adapted to pressurize blood entering the pumping chamber for exiting at the blood outlet. The impeller can have one or more magnetic regions. The impeller can be radially and axially suspended in rotation by magnetic forces created by passive and active sources of magnetic flux acting upon the impeller. One or more hydrodynamic thrust bearings may be provided on an upper surface of the impeller.

The housing assembly may have an upper or front casing and a rear or lower casing. When assembled, the housing defines a substantially cylindrical pumping chamber and a volute having a tangential blood outflow port. In one embodiment, a relatively short axial inflow cannula can be integrated with the upper casing and is adapted for insertion into a ventricle of the heart. The outflow port can be directed perpendicular to the axis of the inflow cannula.

The blood inflow cannula may be straight, curved or otherwise bent to facilitate the fit of the blood pump into the thoracic cavity of the patient or to improve blood flow characteristics.

An electromagnetic motor for driving the pump may include fixed electromagnetic stator portions outside the blood flow region and a rotor comprising an impeller within the pumping chamber adapted to create fluid pressure within the pumping chamber so that blood moves from the inflow to the outflow port. In one embodiment, the motor is a dual stator axial flux gap design with the impeller located within the pumping chamber between spaced apart motor stators. An upper motor stator can be located adjacent to or on the upper or front casing and a lower motor stator can be located adjacent to the lower or rear casing. Each motor stator may contain a plurality of electrical coils or windings arranged on a substantially circular iron core member for electromagnetic coupling with corresponding magnetic regions of the impeller to cause the impeller to rotate within the pumping chamber. The upper motor stator may be positioned closer to the impeller than the lower motor stator. In such way, the upper motor stator may impose an axial magnetic preload on the impeller to counter the magnetic impact on the impeller of the lower motor stator. In some situations a single stator may be placed on or adjacent to the upper casing for the same purpose. In one embodiment, each motor stator is co-axial with the rotational axis of the impeller. The impeller and each motor stator can be essentially circular in horizontal cross section and may have substantially the same diameter to aid in radial stiffness of the rotating impeller during operation of the pump.

The impeller may have a substantially circular circumference and may be formed from a ferromagnetic substance. Ferromagnetic substances may be materials that are strictly ferromagnetic as well as materials that are ferromagnetic. A suitable ferromagnetic substance may be, for example, compression bonded neodymium or Alnico (aluminum-nickel alloy). A ferromagnetic impeller allows for the magnetization of various regions of the impeller in a desired configuration. A ferromagnetic impeller may be treated with a conformal, protective polymer coating of an organic polymer such as Parylene, or silicone, to prevent oxidation by forming a hermetic seal around the rotor. On top of this, a hard, lubricious protective coating may be applied over the conformal polymer coating, to protect against wear and abrasion. Such coatings may include chromium nitride, titanium-nitride, or other commercially available coatings such as ME92, Med Co 2000, or DLC.

A suitable ferromagnetic substance may be biocompatible. For example, a platinum-cobalt alloy may be used. Where the magnet material is biocompatible, the impeller may not need to be coated with a biocompatible material.

In one embodiment, the impeller can include a plurality of solid or hollow bodies having a combination of plane and curved surfaces, the bodies being spaced apart around the impeller periphery. The outer peripheral side wall of each of the bodies can be convex in the radial direction with a radius of curvature that corresponds to the overall circular circumference of the impeller. The plane surfaces are flat, and two straight side walls are of unequal length. The side walls of unequal length may extend radially inwardly from the convex peripheral side wall of the body to intersect at angle of approximately 60 degrees. The impeller bodies may be similarly shaped. In each case the volumes of each impeller body may increase from the point of intersection of the two straight side walls to a convex peripheral side wall. The impeller can be centrally open thereby defining an axial blood flow passage to the bottom wall of the pumping chamber. The intersecting side walls of the impeller bodies may project somewhat radially into the open center of the impeller. The intersections are rounded to minimize thrombosis and hemolysis. The bodies are interconnected at their side walls by support bars, the radial peripheral edges of which are convex with a radius of curvature that corresponds to that of the convex side walls of each of the impeller bodies and which, together with the convex side walls of the impeller bodies define the circular circumference of the impeller. The impeller bodies may protrude axially upwardly and downwardly on both sides of the interconnecting support bars and define substantially parallel upper and lower projection surfaces 26, 26A respectively. The upper and lower projection surfaces may be magnetized to interact with magnetic forces imposed by the motor stators to permit the impeller to be rotated within the pumping chamber. The lower projection surfaces 26A of the impeller bodies can be substantially flat, and can be smooth and parallel to the bottom wall of the pumping chamber. In one embodiment, the inner to outer dimension of each support bar is not greater than half of the inner to outer dimension of the side walls of the adjacent impeller bodies to which it is affixed or with which it may be integrally formed. The arcuate length of each support bar defines the width of a blood flow path between adjacent impeller bodies. Each flow path between adjacent impeller bodies can be substantially uniform in circumferential width. The longer side wall of one impeller body may face the shorter side wall of an adjacent impeller body across a support bar. The longer and shorter side walls can define the sides of each of the fluid flow paths. In such embodiment, the longitudinal axis of each flow path can define an angle with the longitudinal axis of each of the flow paths adjacent to it on either side of approximately 60 degrees.

Alternatively, the impeller bodies may be formed as hollow titanium casings. Each such casing can define an interior cavity which may be fitted with a permanent magnet. Each inserted magnet is held within its associated cavity by a cap element that is hermetically sealed to the casing, such as by laser welding.

The impeller may be magnetically and hydrodynamically suspended from contact with the pump housing both radially and axially when the pump is operating. Hydrodynamic axial thrust forces on the impeller may be created during operation of the pump by a bearing surface inclined or tapered in the axial direction. Such bearing surface can be formed on at least one of the projection surfaces of the impeller bodies adjacent to an internal surface of the upper pump casing. In some embodiments, one of such bearing surfaces may be formed on each of the upper projection surfaces. As the impeller rotates, blood may engage a tapered bearing surface at a relatively low pressure entrance end and creates sufficient pressure to move the impeller axially as the impeller rotates. A pressure relief surface may optionally be formed downstream of and adjacent the exit end of each inclined bearing surface. The pressure relief surface may be tapered in an axial direction to diverge oppositely to the slope of the inclined bearing surface. Such pressure relief surface may thereby form an area of lower fluid pressure to avoid hemolysis during operation of the pump.

In one embodiment, the motor stators can be concentric with the impeller and have substantially the same diameter. In such way, magnetic interaction between the motor stators and magnetic regions of the impeller may assist in creating radial impeller stiffness. Axial preload on the impeller may be provided by locating a motor stator on the upper pump housing casing in close proximity to the impeller. In a dual motor stator embodiment, axial preload on the impeller may be provided by locating the upper motor stator closer to the impeller than the lower motor stator.

Magnetic preload can enable the impeller to avoid contact between its bottom surfaces and the lower interior surface of the lower pump housing casing. During operation, the axial force produced by hydrodynamic thrust bearing surfaces on the upper projection surfaces of the impeller bodies can move the impeller away from the upper wall of the housing but permits a blood flow path between the lower projection surfaces of the impeller and the lower wall of the housing. Fluid pressure within the pumping chamber keeps blood in motion below the impeller. Blood may move from beneath the impeller up through the open center of the impeller as the impeller rotates.

In one embodiment, as a result of preload and hydrodynamic forces acting in axially opposite directions on the impeller and the unique structure of the impeller, the impeller may be effectively dynamically suspended between the upper and lower casings of the pump housing during operation of the pump. Blood is thereby forced to move about the impeller and through the pumping chamber without hemolysis or thrombosis. It will be understood that magnetic forces may be provided by permanent magnets, by electromagnetic circuits, by magnetization processes or by a combination of such sources of a magnetic flux field.

A method of operation in accordance with an embodiment of the invention can include apical implantation of a short inflow cannula into the left ventricle of a heart, pressurizing the inflowing blood fluid within a pumping chamber by causing rotation therein of an impeller without mechanical contact with the impeller, positioning the rotating impeller to be suspended within the chamber so as to be completely submerged in the inflowing blood fluid, causing the inflowing blood fluid to traverse a plurality of flow paths formed within and around the impeller whereby pressure within the pumping chamber causes continuous flow of the blood from the inflow to an outflow from the pumping chamber, and directing the outflowing blood through a tube graft to the aorta.

BRIEF DESCRIPTION OF THE DRAWINGS

For a further understanding of the present invention, reference may be had to the accompanying drawings from which the nature and attendant advantages of the invention will be readily understood, and in which.

DETAILED DESCRIPTION

Figure 1:
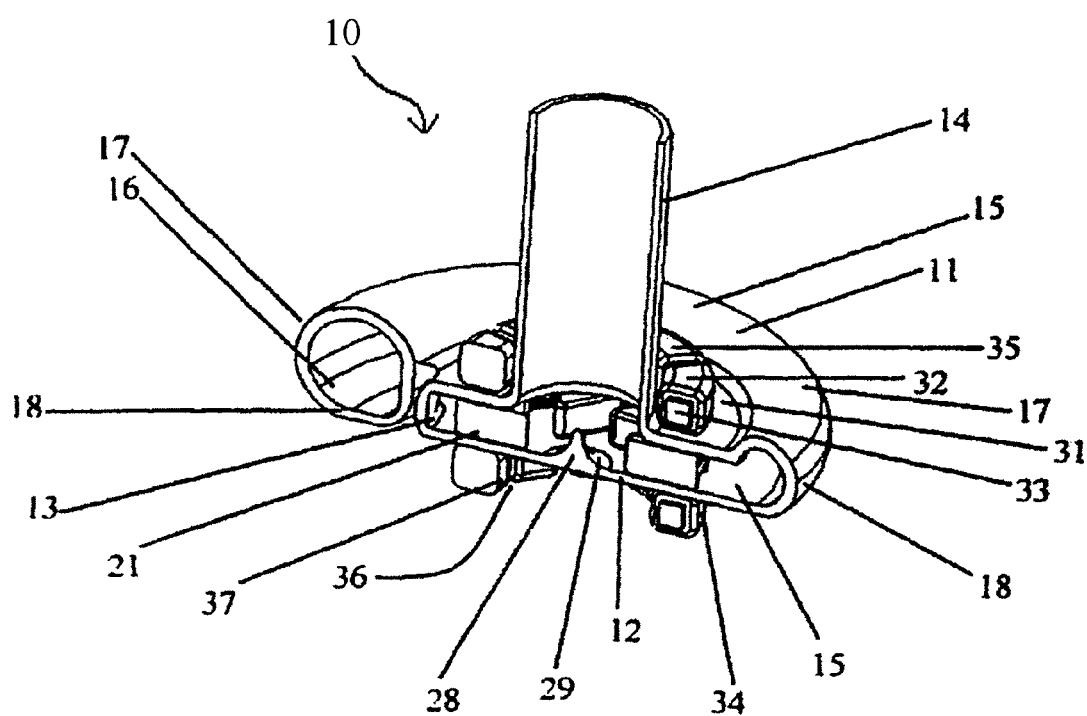
FIG. 1 is a cross-sectional perspective view of a rotary blood pump according to a dual motor stator embodiment of the present invention.

In describing the embodiments of the present invention illustrated in the drawings, specific terminology is employed for sake of clarity. However, the present disclosure is not intended to be limited to the specific terminology so selected, and it is to be understood that each specific element includes all technical equivalents that operate in a similar manner.

Embodiments of the present invention provide for small and efficient wearless centrifugal rotary blood pumps having hydrodynamic and magnetic thrust bearings for axial and radial stiffness and improved continuous fluid flow paths within the pump to diminish the risks of hemolysis and thrombosis in the blood being pumped. Other examples of similar blood pumps can be found in U.S. Provisional Patent Application 60/758,793 ("the '793 application"), filed Jan. 13, 2006, the disclosure of which is herein incorporated by reference. It is intended that features disclosed herein may be combined with features disclosed in the '793 application. In one embodiment, hydrodynamic thrust bearing surfaces of the impeller may be used to constrain the position of the impeller in a direction of the axis of rotation of the impeller without requiring a cooperative constant polarity magnetic force to be exerted in an axial direction from a fixed position with respect to the housing. In such case, no permanent magnet may need to be affixed to the housing of the pump for the purpose of exerting an axially directed constant polarity force on the impeller.

Figure 2:
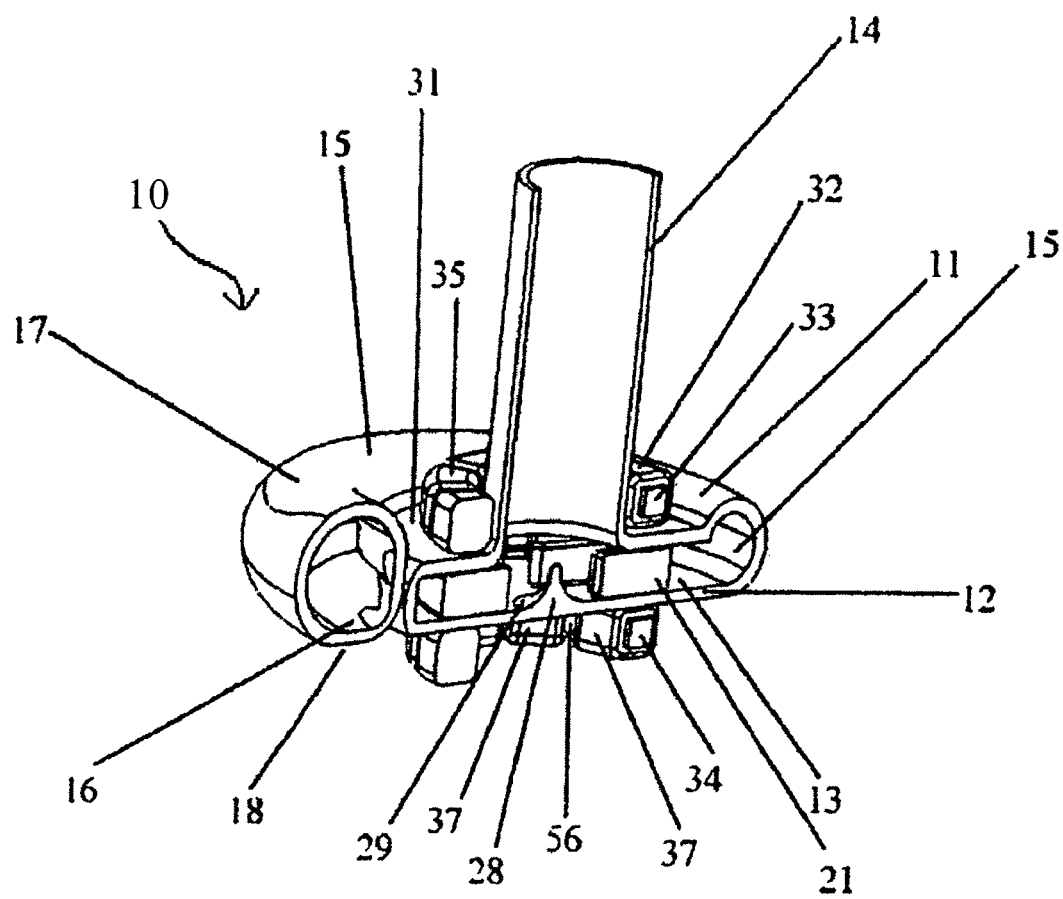
FIG. 2 is cross-sectional perspective view of the rotary blood pump FIG. 1 from a different perspective.
Figure 3:
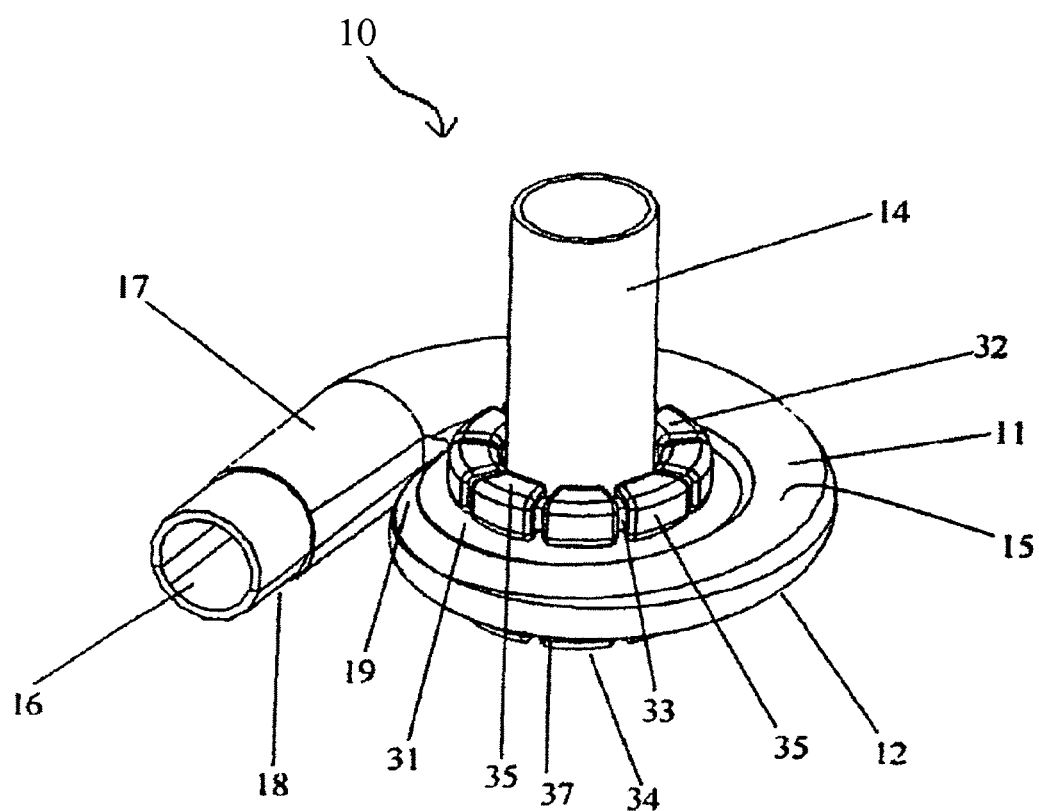
FIG. 3 is a perspective view of the rotary blood pump embodiment of FIG. 1.

Referring now to FIGS. 1-3, there is shown a rotary centrifugal blood pump 10 having a pump housing that consists of a substantially circular front or upper pump casing 11 and a substantially circular rear or lower pump casing 12 of equal diameter that interlocks with the upper pump casing 11 to form a pumping chamber 13 having a substantially rectangular cross section in a vertical plane. The upper pump casing 11 may have a plurality of peripheral positioning holes [not shown] for receiving a corresponding plurality of positioning pins [not shown] projecting from the periphery of the lower pump casing 12. The configuration of positioning holes and positioning pins ensures that the upper pump casing 11 and the lower pump casing 12 interlock in the correct position when the rotary blood pump 10 is assembled. The contact area between the upper pump casing 11 and the lower pump casing 12 may be sealed, for example, using screws or a chemical sealant.

In the embodiment shown in FIG. 1, blood is supplied to the pump through an axial inlet cannula 14 adapted for apical insertion into a heart ventricle. The cannula 14 is affixed to or may be integral with the upper pump casing and is in fluid flow communication with the pumping chamber 13.

A rotatable impeller 21 is arranged within the pumping chamber 13 with its rotational axis concentric with the longitudinal axis of the cannula 14. In one embodiment, the pumping chamber is in fluid-flow communication with a volute or diffuser 15 to avoid alteration of the position of the impeller in a radial direction as blood pressure increases during operation of the pump. The upper pump casing 11 and lower pump casing 12 together define the diffuser 15 by a pair of complementary upper and lower half-round sections 17 and 18 formed as part of the upper and lower housing casings, respectively. The diffuser 15 extends completely around the circumference of the pump terminating at a tangential outlet port 16. Blood exits the pumping chamber 13 through the outlet 16 in a direction substantially perpendicular to the longitudinal axis of the inlet cannula 14, an arrangement that has been found to be anatomically advantageous for locating the pump in the pericardial space. In the embodiment of FIGS. 1-4A, the cross section of the diffuser 15 enlarges from an inlet end 19 along its length to a maximum at the outlet 16. When the pump is installed and in operation, the outlet 16 is adapted to be joined to a blood conveyance graft [not shown] which, in turn, is suitably connected to the aorta.

Sealing of the cannula 14 to the heart ventricle may be accomplished with the assistance of a peripheral ring groove [not shown] formed in the outer cylindrical surface of the cannula near the upper pump casing 11. The ring groove is fitted with an annular O-ring to provide a leak proof seal to a sewing ring of a ventricular connector [not shown] of the type described, by way of example, in commonly owned U.S. Pat. No. 6,732,501. According to another embodiment, a peripheral ring groove is unnecessary and an O-ring surrounding the cannula may be incorporated into the sewing ring to ensure a leak proof seal.

The pump housing and the cannula may be made of titanium, a biocompatible titanium alloy, or a biocompatible ceramic material. The pump structure may be machined from titanium or an alloy thereof. Alternatively, the pump structure may be formed entirely from ceramic material.

With reference to FIGS. 1, 2, and 7-10C, the impeller 21 is located within the pumping chamber 13 between the upper pump casing 11 and the lower pump casing 12. In one embodiment, the impeller 21 has a circular cross section which, by way of example, may have a 1-inch diameter. To minimize the weight of the impeller it may be open in its interior, as at 22, seen best in FIGS. 9A-9C. The open interior of the impeller permits a direct axial passage for blood from the inlet cannula through the impeller to the bottom of the pumping chamber, defined by an interior wall of the lower pump casing 12. In one embodiment, the cross section of the open interior of the impeller is at least as large as the cross section of the inlet channel of the cannula.

In operation, blood entering the cannula 14 from a heart ventricle passes axially into the pumping chamber 13 where it is engaged by the rotating impeller. The rotating impeller causes blood pressure to build to a maximum at the outlet 16. Referring to FIGS. 1, 2, 7, and 14, in one embodiment, a central nub or post 28 extends axially upwardly from the center of the bottom wall of the pumping chamber. The post 28 is provided with a conical upper surface 29 over which blood entering the pumping chamber from the cannula 14 flows and is redirected from axial flow exiting the cannula to a radial flow within which the impeller 21 is submerged. Blood is pressed radially into a whirling motion as a result of the configuration of the spinning impeller, described in detail below, and moves within the diffuser 15 at the perimeter of the pumping chamber to the outlet 16.

The blood pump is driven by an external electromagnetic drive motor. In one embodiment, the drive motor for the impeller consists of an upper motor stator 32 and a lower motor stator 34, shown in each of FIGS. 1-4A, 5, 7, 8, and 15. The upper stator 32 has a substantially annular central iron core 33 around which a plurality of spaced-apart coil sections 35 are placed. As shown in FIGS. 1-3 and 6, the upper stator 32 is positioned on a substantially flat annular outer surface 31 of the upper pump casing 11 and closely surrounds the cylindrical cannula 14 above the pumping chamber 13. The upper stator 32 is thereby in close proximity to and concentric with the impeller 21, but separated from the impeller by the top wall of the upper pump casing 11 so that the upper stator 32 does not contact the blood within the pumping chamber 13. The lower stator 34 also consists of a substantially annular iron core 36 around which a plurality of spaced-apart stator coil sections 37 are placed. The lower stator 34 is positioned under the bottom wall of the pumping chamber 13 and is concentric with both the impeller 21 and the upper motor stator. In one embodiment, the diameters of the upper stator 32, the lower stator 34 and the impeller 21 are substantially the same. An advantage of a dual stator motor is that one of the stators may be used to cause the impeller to rotate should the other stator fail to function. In one embodiment, the lower stator 34 is spaced farther from the impeller 21 than the upper stator 32 so as not to degrade a net axial preloading of the impeller resulting from its magnetic interaction with the upper stator 32, as described below.

Figure 12:
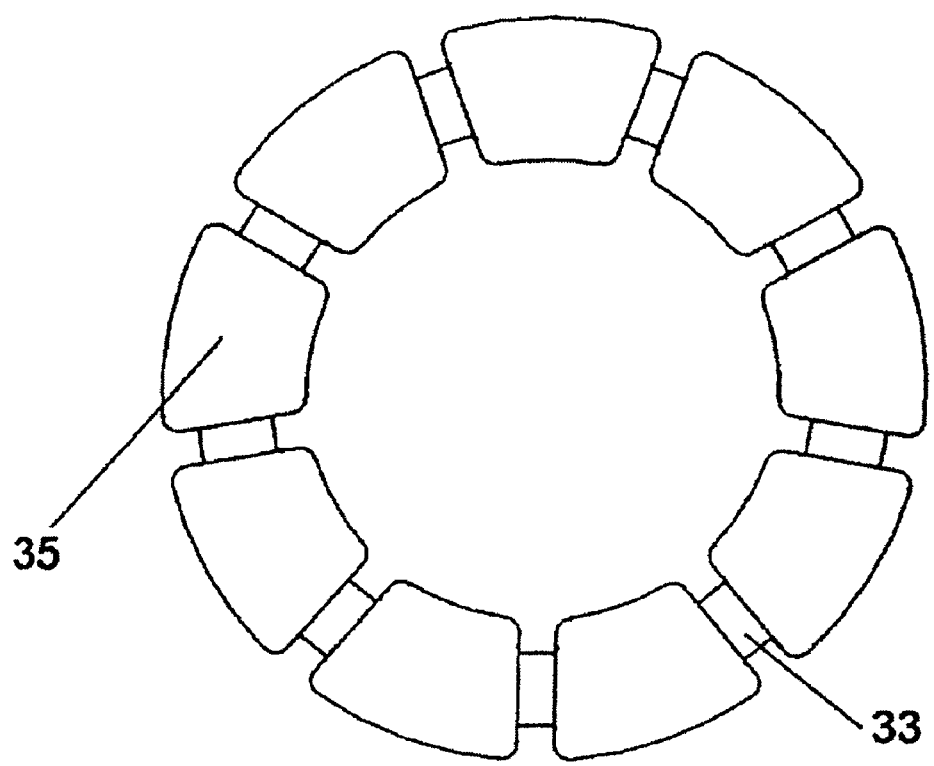
FIG. 12 is a top plan view of a motor stator according to an embodiment of the present invention.

FIG. 12 is representative of each of the upper and lower motor stators. As illustrated, each motor stator contains the plurality of the motor drive coils or windings, represented in FIG. 12 as coil 35 of the upper motor stator. In one embodiment, nine such coils are spaced apart respectively around the annular central iron cores, represented in FIG. 12 as core 33 of the upper motor stator. It will be understood that the number of coils forming the motor stators may vary without departing from the scope of the present invention. The motor drive windings consist of coils of electrically conductive wire arranged to produce magnetic poles that are cyclically changed by electrical pulses to provide a rotating magnetic field. As will be understood by those skilled in the art, the electromagnetic poles interact with magnetic fields from the impeller to cause the impeller to rotate. The magnetic forces produced by the motor stator coils also provide secondary radial impeller and axial magnetic preloading support to the impeller. The result is that the impeller is dynamically balanced in both the radial and axial directions during normal operation.

Figure 4A:
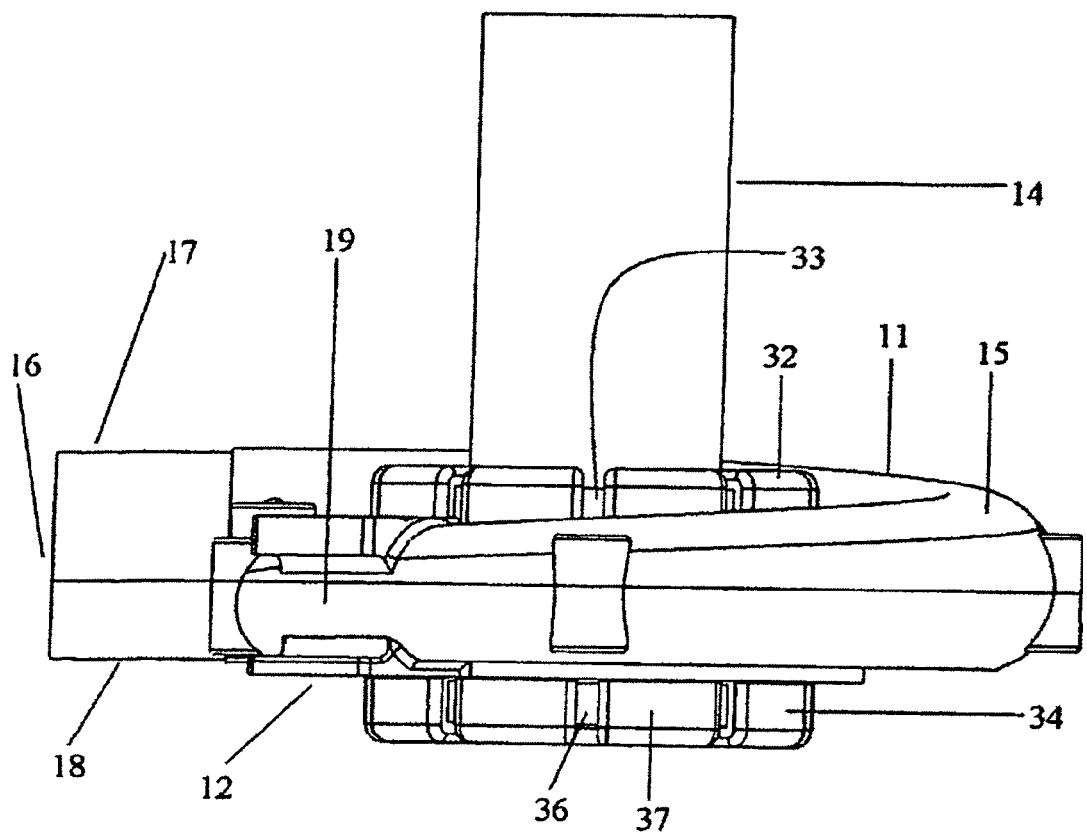
FIG. 4A is a side elevation of the blood pump embodiment of FIG. 1.
Figure 4B:
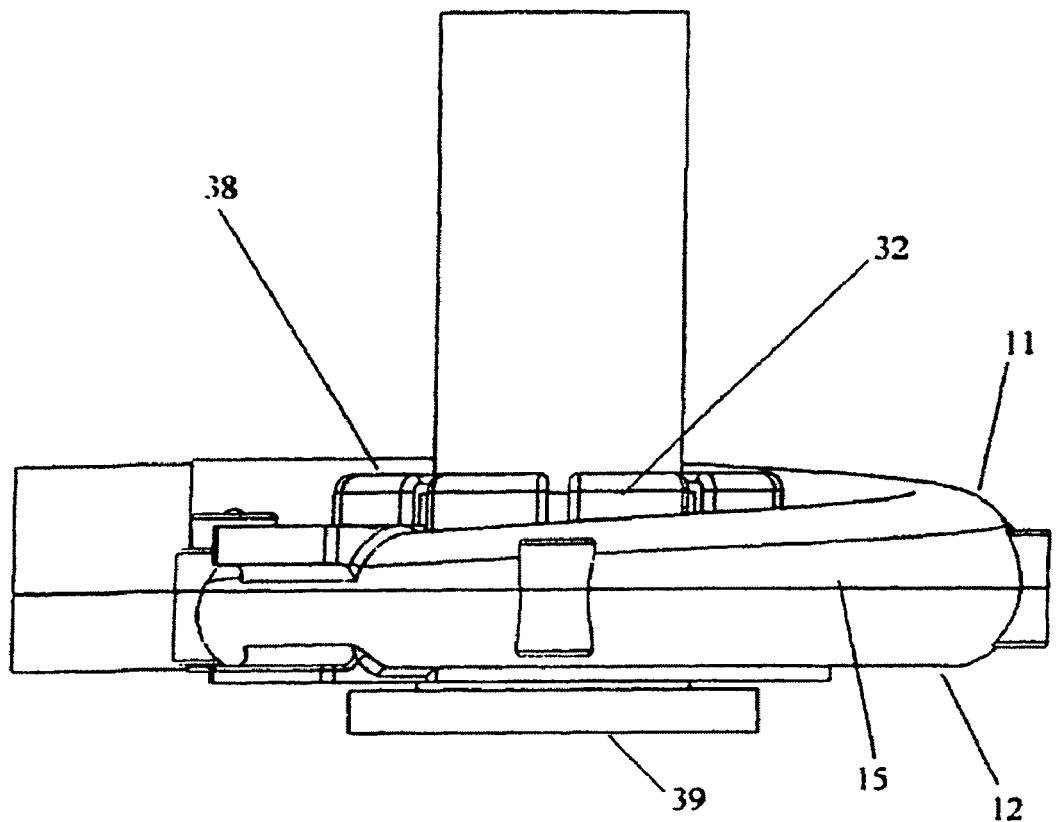
FIG. 4B is a side elevation similar to FIG. 4A of a rotary blood pump having a single motor stator.
Figure 5:
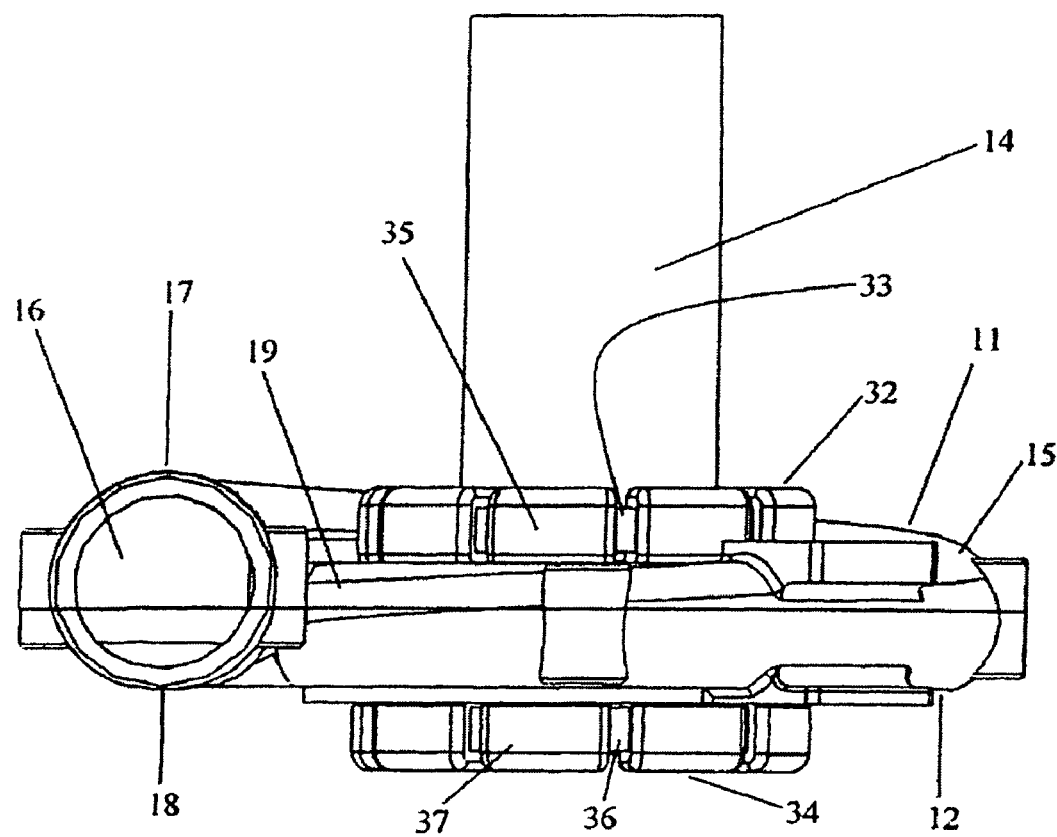
FIG. 5 is a different side elevation view of the rotary blood pump of FIG. 4A.
Figure 6:
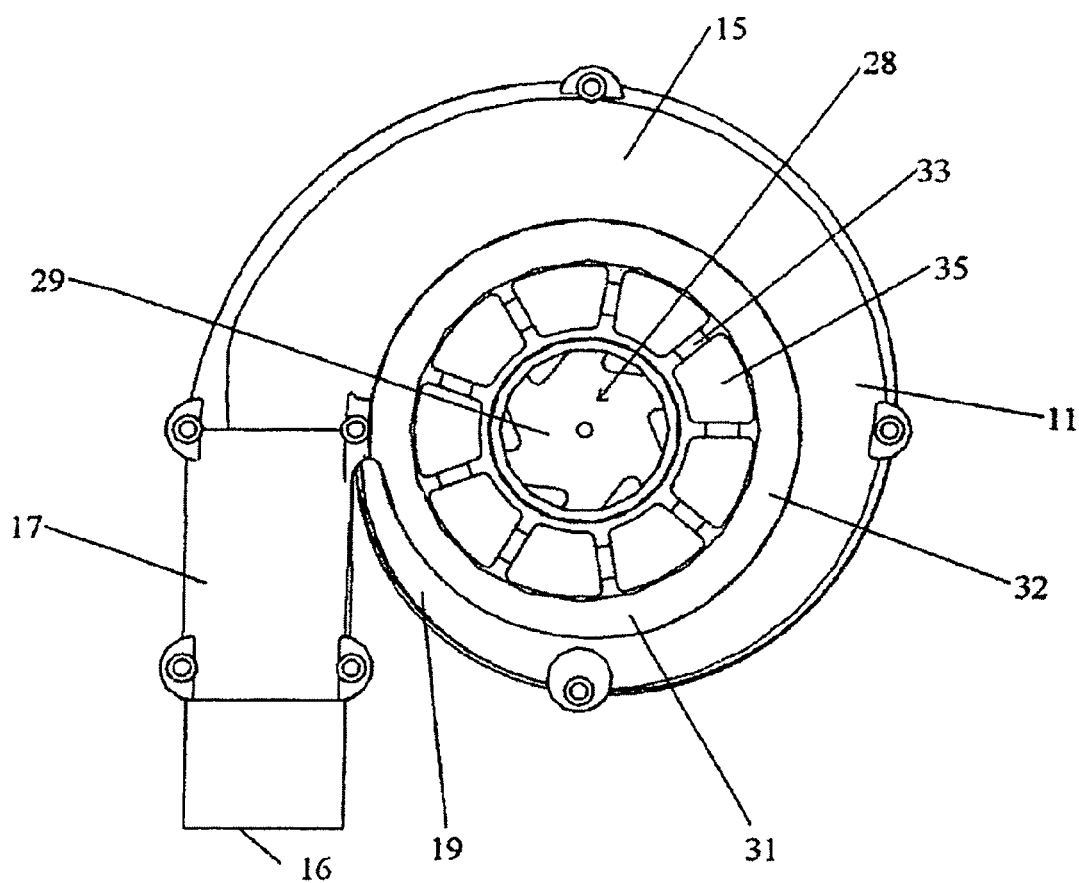
FIG. 6 is a top planar view of the rotary blood pump of FIG. 1, partially cut away to show the central portion of the interior of the pumping chamber.
Figure 7:
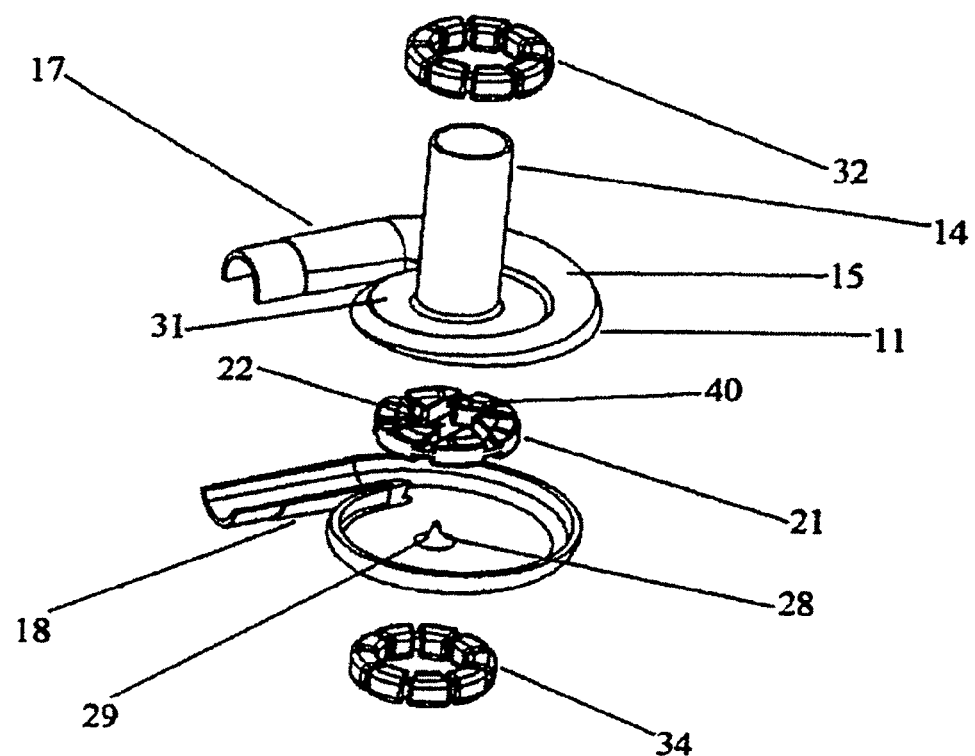
FIG. 7 is an exploded upper perspective view of the rotary blood pump of FIG. 1.

It will be understood that only a single motor stator is needed to operate the pump motor of the present invention. With reference to FIG. 4B, there is shown a drive motor for a centrifugal pump similar to the pump of FIG. 1 in which there is only a single annular motor stator 38 located on the upper surface of the upper pump casing 11. The single motor stator 38 is configured substantially the same as motor stators 32 and 34. When a single motor stator is used, an annular iron back ring 39 is provided beneath the bottom wall of the pumping chamber. The back ring 39 is substantially concentric with both the impeller within the pumping chamber and the motor stator 38 for closing a magnetic flux circuit induced by the stator 38 during operation of the pump.

The magnetic flux generated by the upper motor stator may be designed to interact with magnetized areas of the impeller or permanent magnets embedded in the impeller. In one embodiment, the magnetic coupling between the upper motor stator and the impeller tends to provide a magnetic preload on the impeller to bias the impeller away from the bottom wall of the pumping chamber while, at the same time, tending to cause the impeller to rotate. Such magnetic coupling also promotes radial stability of the impeller during operation of the pump. It will be understood that other magnetic bearing configurations may contribute to axial and radial support and stability of the impeller without departing from the scope of the present invention.

Figure 8:
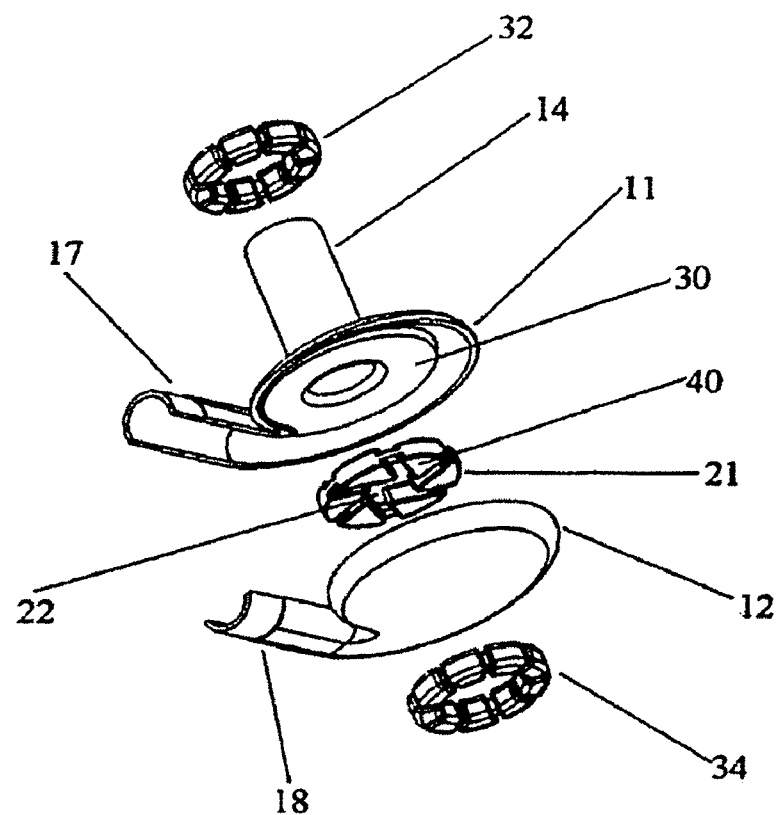
FIG. 8 is exploded lower perspective view of the rotary blood pump of FIG. 1.
Figure 9A:
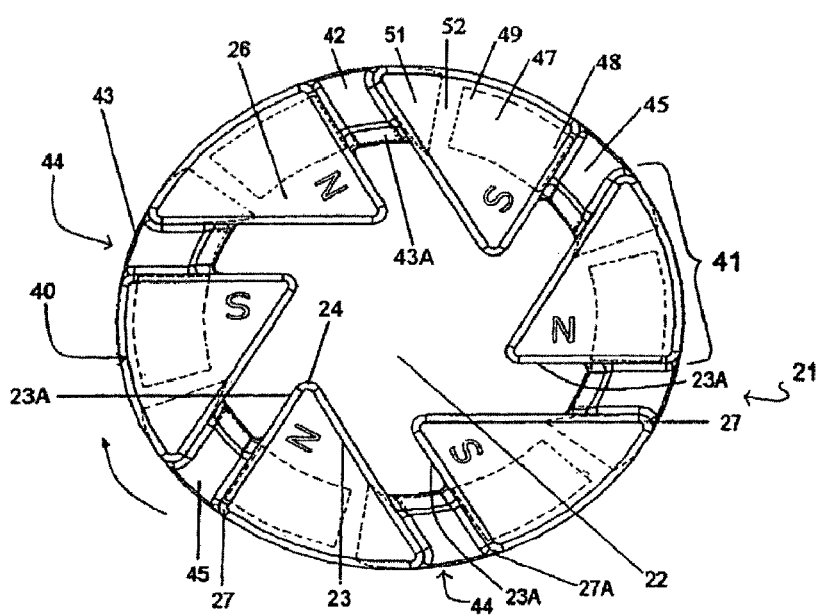
FIG. 9A is a top planar view of an impeller magnetized and having hydrodynamic thrust bearing surfaces according to one embodiment of the present invention.
Figure 9B:
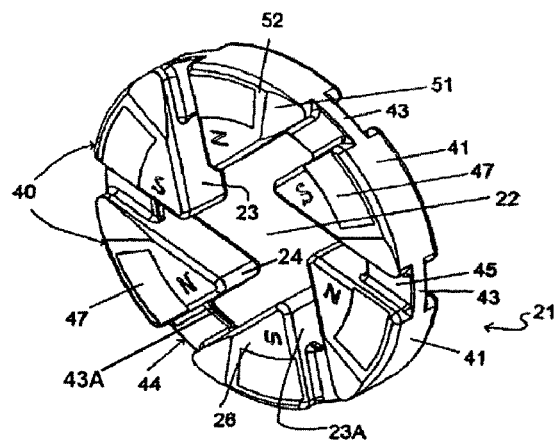
FIGS. 9B and 9C are perspective views of the impeller of FIG. 9A showing the upper surfaces and lower surfaces of the impeller, respectively.
Figure 9C:
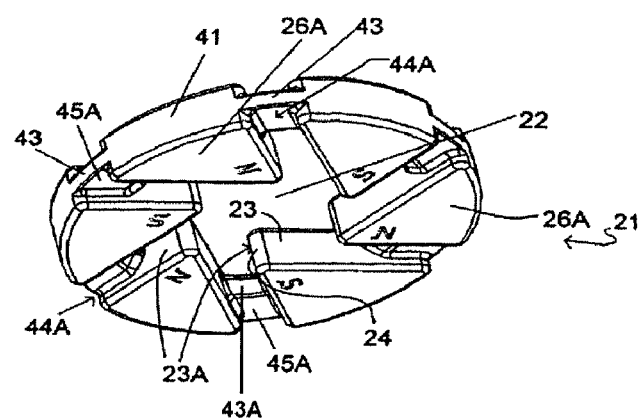
Figure 9D:
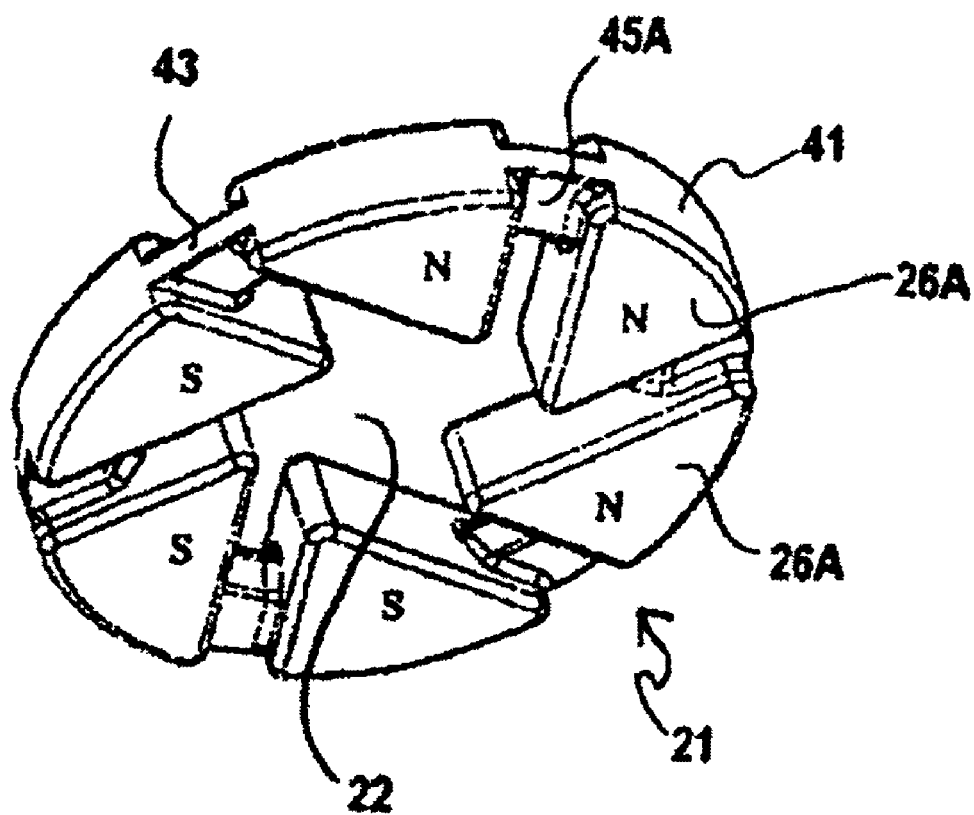
FIG. 9D is a perspective view of the lower surfaces of an impeller magnetized according to another embodiment of the present invention.
Figure 14:
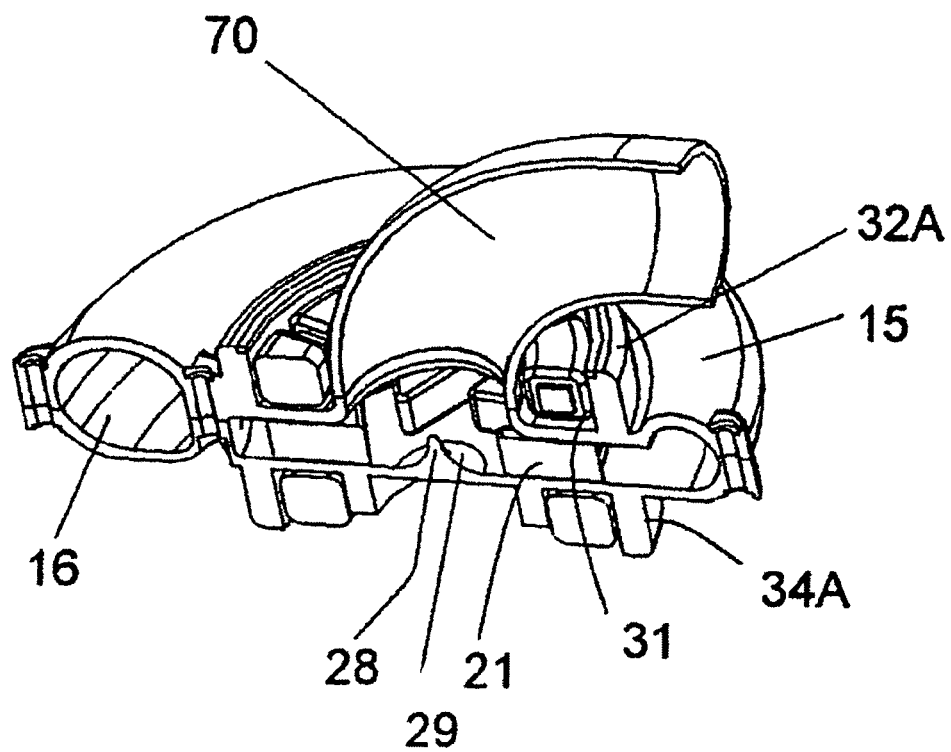
FIG. 14 is a cross-sectional perspective view of a rotary blood pump with a curved inflow cannula according to another embodiment of the present invention.
Figure 15:
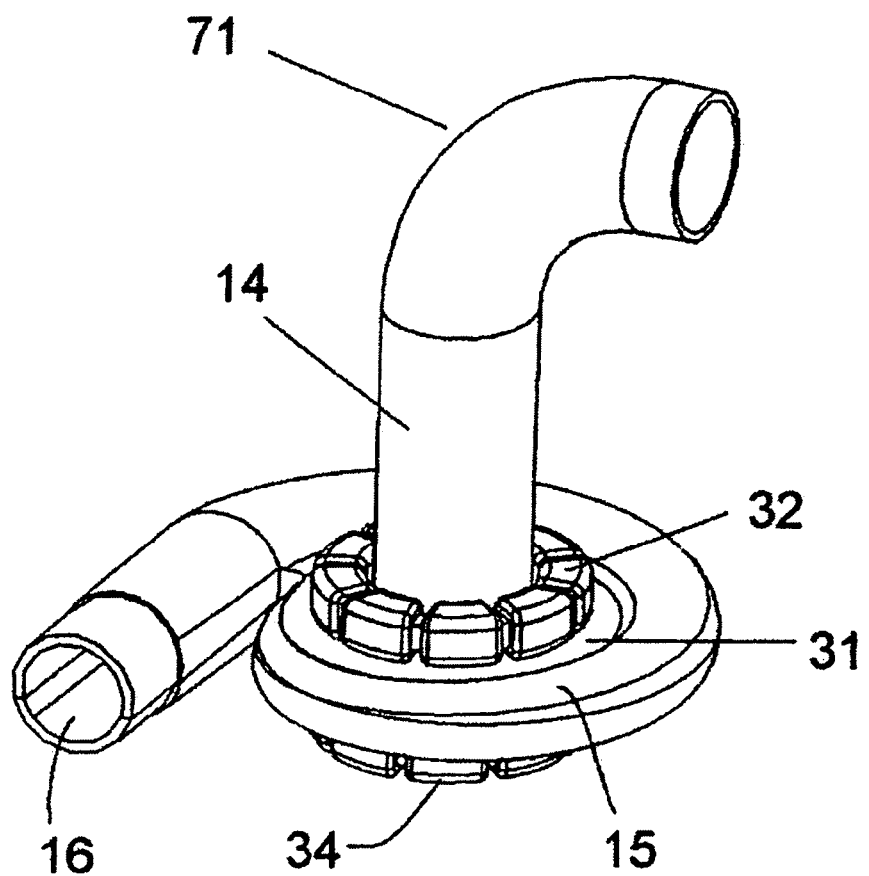
FIG. 15 is a perspective view of a rotary blood pump having a bent inflow cannula according to another embodiment of the present invention; and, FIG. 16 is a perspective view of an alternate embodiment of the impeller in accordance with the present invention.

With reference to FIG. 14, the upper and lower motor stators may be enclosed within respective casings 32A, 34A integral with respective upper and lower pump housings and defining annular channels within which to seal respective motor stators 32 and 34. Side walls for the motor stator casings may be integral with the pump housing and made of a biocompatible material. Annular caps [not shown] may be hermetically sealed to the motor stator casings. Alternatively, each motor stator may be contained within a stator can separately affixed to the pump housing [not shown]. In one embodiment, the top wall of the pumping chamber, on the outside of which the upper motor stator 32 resides, may be thin, for example, less than 0.007 inches thick in an area closest to the impeller. With reference to FIG. 8, such a thin wall allows the use of a ceramic disc insert 30 on the inner surface of the top wall of the pumping chamber between the impeller and the upper motor stator. The ceramic disc facilitates start up of the pump and minimizes wear on the upper surfaces of the impeller. Alternatively, as indicated above, the pump housing may be made from suitable ceramic material, in which case the ceramic disc insert 30 would not be required.

Each motor stator casing or stator can has a hermetically sealed feed-through arrangement for electrical wires to connect the stator coils or windings to external headers or connectors [not shown]. In one embodiment, the feed-through wires are platinum. The headers connect the feed through wires to external drive cables. The header may be made of a material such as PEEK or a suitable plastic such as Tecothan or polysulfone. The header may also be made of a medical grade epoxy.

Referring now to FIGS. 9A-9D, an impeller 21 according to an embodiment of the present invention is shown in greater detail. In this embodiment, the impeller 21 is circular in cross section and consists of a plurality of interconnected solid impeller bodies 40 spaced apart and defining a portion of the impeller periphery. There may be from two to eight such impeller bodies. Each of the impeller bodies 40 has a substantially triangular configuration as seen from the top, and comprises a convex circumferential side wall 41 defining a portion of the overall circular circumference of the impeller. The remaining two side walls 23, 23A of each of the bodies 40 are of unequal length and extend radially inwardly of the circumference of the impeller to intersect at an angle of approximately 60 degrees. The intersection of the side walls 23, 23A is a rounded inner edge 24. As the impeller rotates in the direction shown by the arrow in FIG. 9A, the shorter side wall 23A of each of the impeller bodies 40 constitutes a leading surface in the direction of rotation, while the longer side wall 23 constitutes a trailing surface. Each of the inner edges 24 of the impeller bodies is forward of the outer edges 27, 27A such that when the blood is engaged by the shorter side walls 23A it is pressed radially outwardly between adjacent bodies into a somewhat whirling motion around the impeller and within the volute or diffuser 15 (FIG. 1).

Adjacent impeller bodies 40 are interconnected by support bars 42. The outer peripheral edge 43 of each of the interconnecting support bar [seen best in FIGS. 9B and 9C] is curved convexly to coincide with the circumferential circle of the impeller. Inner peripheral edges 43A [FIG. 9A] of each of the support bars are congruent with the outer peripheral edges 43. Upper and lower surfaces 45, 45A respectively of each of the support bars [FIGS. 9A and 9C] define the bases for upper and lower fluid flow paths 44, 44A through which blood passes during operation of the pump. The width of each flow path is coextensive with the arcuate width of each support bar. The longer side wall 23 of each impeller body is substantially vertical and faces the substantially vertical shorter side wall 23A of an adjacent impeller body across the arcuate width of the support bar to define the sides of each of the fluid flow paths. In one embodiment, the longitudinal axis of each flow path defines approximately a 60 degree angle with the longitudinal axis of each of the flow paths adjacent to it on either side. The impeller bodies 40 protrude axially above and below the support bars 42 and accordingly the longer side wall 23 and the shorter side wall 23A of each of the impeller bodies 40 also extends above and below the support bars 42. As described above, the leading shorter side wall 23A presses blood radially outwardly over the flow paths between the impeller bodies both above and below the support bars 42.

The impeller may be a single integral structure made of a magnetically isotropic alloy. In that event, each impeller body 40 may have a magnetized portion. In one embodiment, the upper and lower projection surfaces 26 and 26A may be magnetized to provide magnetic poles. As indicated, the magnetic poles of the impeller couple magnetically with magnetic poles provided by the motor stators 32 or 34, thereby enabling one or both of the stators to provide both a magnetic drive force to cause the impeller to rotate within the pumping chamber and magnetic axial and radial support. In one embodiment, as seen in FIGS. 9A and 9B, and 10A and 10B, every other upper projection surface is magnetized to the same magnetic pole while the projection surfaces therebetween are magnetized to have the opposite magnetic pole. For example, where an upper projection surface has a north magnetic pole each projection surface on either side has a south magnetic pole. In such an embodiment, the lower projection surfaces 26A of the drive bodies 40 are suitably magnetized with alternating polarities.

It will be understood that where magnetized projection surfaces of the impeller have alternating polarities, the impeller contains an even number of bodies 40. As a further example, where the impeller has 6 bodies, their projection surfaces on one side of the impeller may be magnetized as north-up, south-up, north-up, south-up, north-up, south-up respectively. Alternatively, as shown by way of example in FIG. 9D, an impeller having six drive bodies may be magnetized such that the magnetized projection surfaces define a contiguous group of three north-up surfaces, that is north-up, north-up, north-up, followed by a contiguous group of three south-up surfaces, or south-up, south-up, south-up. The particular arrangement of magnetic poles may be determined as desired without departing from the scope of the present invention. It will be understood that the motor stator coils that drive the impeller provide magnetic poles in a pattern complementary to those employed on the impeller.

The material of a one-piece impeller of the type described above may be biocompatible to avoid having to coat the impeller or sub-assemblies. An example of a suitable magnetically isotropic biocompatible material is an alloy of approximately 77.6% platinum (by weight) and 22.4% (by weight) cobalt. Such a one-piece impeller may be easier and less expensive to manufacture than impellers formed from multiple parts. Such magnetization may be performed by techniques known in the art, such as the exposure to a relatively strong magnetic field.

Figure 16:
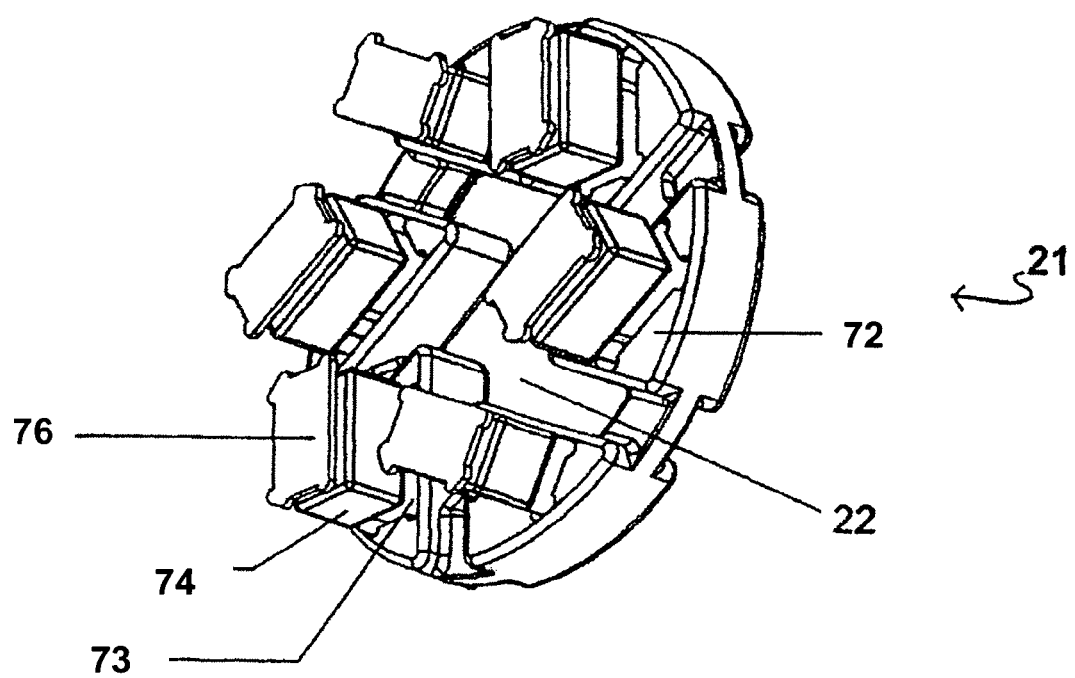

With reference to FIG. 16, the impeller may be formed from titanium in which each of the impeller bodies 40 defines a hollow casing 72 defining a cavity 73. In one embodiment, the cavities 73 are open on the bottom of the impeller. Permanent magnets 74 configured to have slightly smaller dimensions than a respective cavity 73 are inserted into each cavity. A cap 76 configured to enclose the magnet cavity to contain the permanent magnet therein may be laser welded to the block casing to form a hermetic seal between the edges of the cavity and the cap. It will be understood by those having ordinary skill in the art that the cavities may open at the top of the impeller without departing from the scope of the invention. In that event, the cap may be provided with hydrodynamic thrust bearing surfaces as described hereinabove.

Like a magnetized integrally formed impeller of the type described above, the permanent magnets 74 installed within impeller cavities 73 may be selected to provide alternating polarities. Alternatively, the permanent magnets may be selected to form a contiguous group of north-up magnetic poles and a contiguous group of south-up magnetic poles. As indicted, other magnetic configurations may be selected as desired without departing from the scope of the present invention.

Figure 10A:
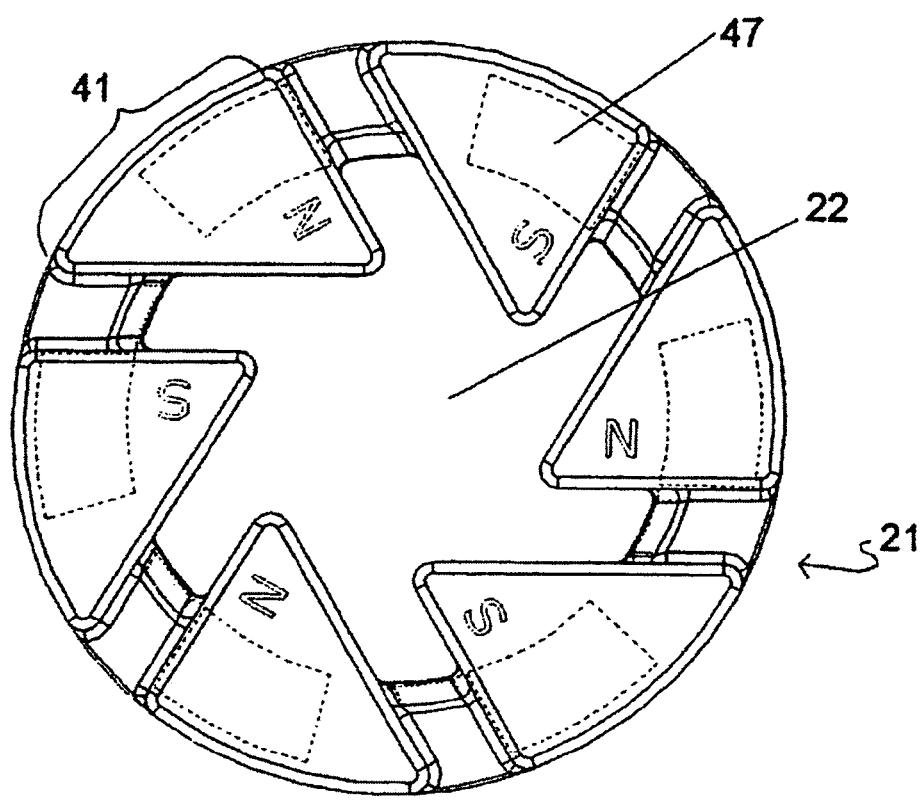
FIG. 10A is a top planar view of an impeller having hydrodynamic thrust bearing surfaces according to another embodiment of the present invention.
Figure 11:
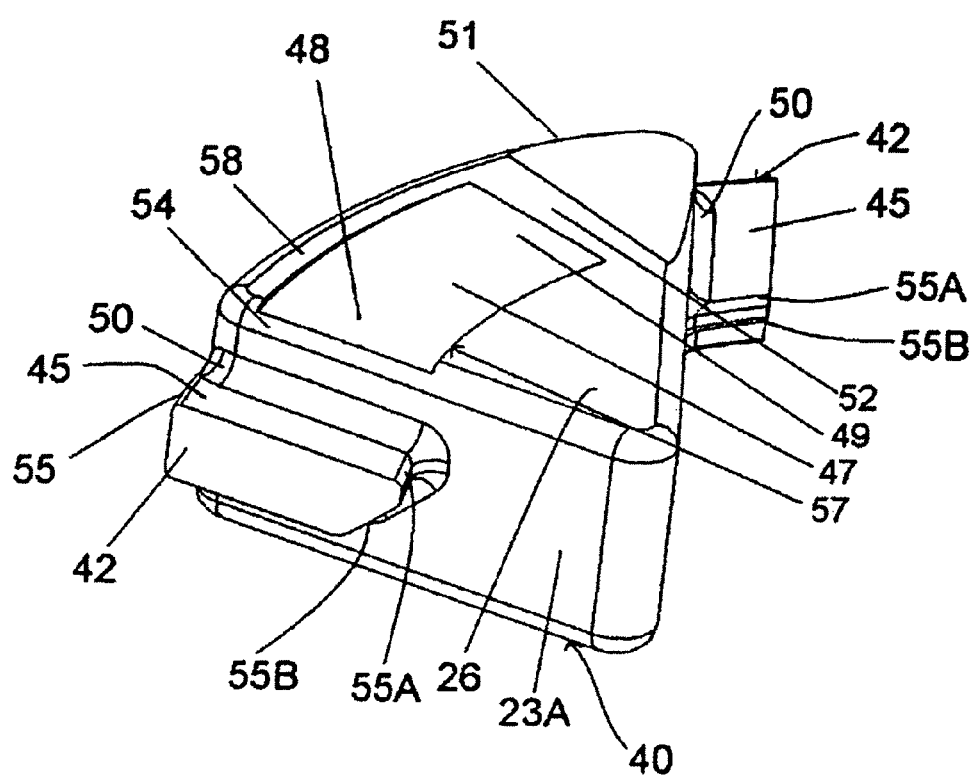
FIG. 11 is a perspective view of a portion of the impeller of FIG. 9A.

With reference to FIG. 11, the upper projection surface 26 of each impeller drive body is provided with a tapered inclined ramp 47 defining an axial hydrodynamic thrust bearing surface. In one embodiment, each bearing surface 47 is inclined upward from a relatively lower fluid pressure entrance region 48 to a relatively higher fluid pressure exit region 49, and curves clockwise in the direction of the exit region 49, as viewed in FIG. 11, or counter-clockwise direction, as viewed in FIGS. 9A and 10A, substantially following the curvature of the circumference of the impeller. The angle of inclination of the bearing surface 47 may be less than one degree relative to the horizontal.

When the impeller 21 is rotating, the gap between the bearing surface 47 and the adjacent ceramic disc 30 on the top wall of the pumping chamber decreases towards the exit region 49. Thus, blood in contact with each bearing surface 47 is compressed with increasing force against the adjacent ceramic disc with result that a net axial downward pressure is exerted on the impeller moving the impeller away from the top wall. The downward pressure on the impeller acts against the upward preload magnetic force from the upper motor stator to suspend the impeller within the pumping chamber as it rotates.

In operation, the rotational speed of the impeller may be within the range of 2,000 to 5,000 RPM. However, the thickness of the blood layer between the bearing surfaces 47 and the adjacent housing surface is a function of the fluid viscosity, the impeller rotational speed and the geometry of the impeller bearing. As the fluid viscosity increases, the fluid layer thickness increases. As the rotational speed increases, the fluid layer thickness increases and, because of the net axial hydrodynamic pressure on the impeller and the fact that the impeller is suspended within the pumping chamber in part by a magnetic preload, the distance from each bearing surface 47 to the adjacent upper casing face can change with rotational speed and fluid viscosity. In one embodiment, that distance in fluid layer thickness will be within the range of from 0.001 inches to 0.003 inches.

Figure 10B:
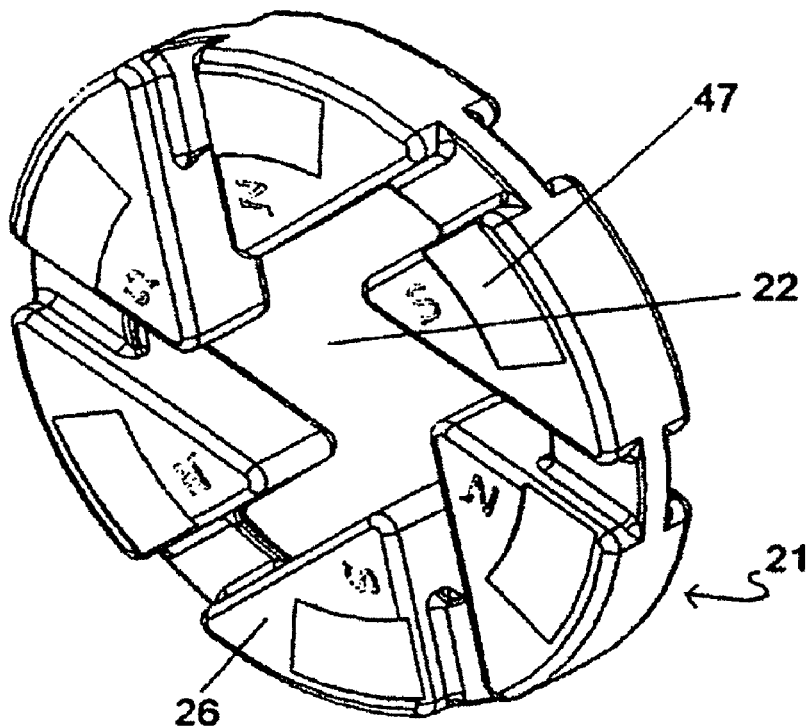
FIGS. 10B and 10C are perspective upper and lower views respectively of the impeller of FIG. 10A.
Figure 10C:
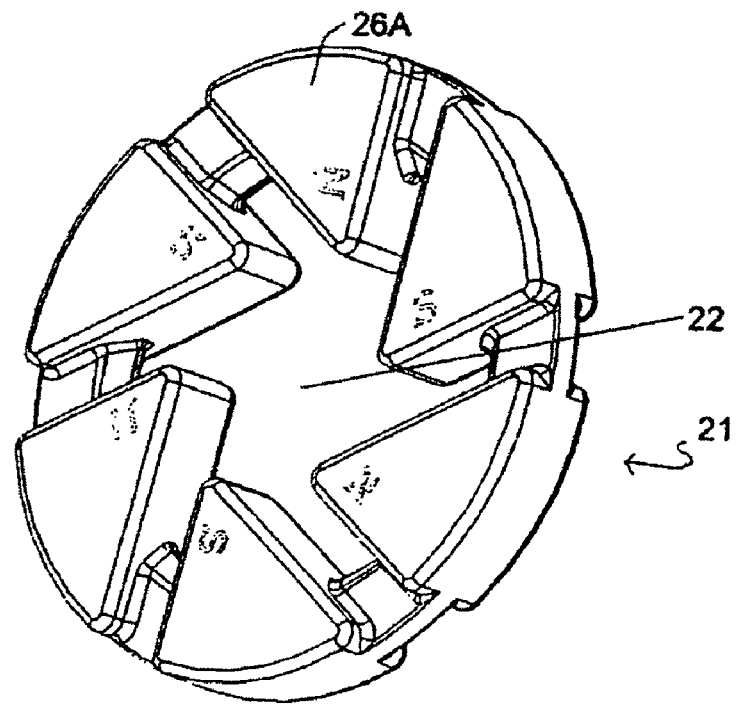

Seen best in FIG. 11, each upper projection surface 26 of each impeller body 40 may, in some embodiments, also have a substantially wedge-shaped region downstream of the bearing surface 47 at its trailing end or exit region 49 that defines a pressure relief surface 51. The pressure relief surface 51 ensures a controlled and predictable lowering of the hydrodynamic thrust pressure to minimize blood shear stress and possible hemolysis. In addition, each pressure relief surface assists in defining a secondary flow path for blood within the pumping chamber whereby blood exiting a thrust bearing surface 47 is re-entrained across the pressure relief surface and into an adjacent fluid flow path 44. A relatively flat bridging area 52 may be formed at the trailing or exit region of each thrust bearing surface 47 between each higher pressure exit region 49 and an associated pressure relief surface 51. In one embodiment, the width of each of the bridging surfaces 52 at its narrowest point is about 0.050 with a reasonable tolerance of ±0.030 inches. In such an embodiment, the pressure relief surface 51 may be inclined relative to the horizontal at an angle of from 2 to 4 degrees. As shown in FIGS. 10A and 10B, some embodiments of the present invention utilize impeller bodies 40 having upper projection surfaces that have the hydrodynamic thrust bearing surface 47 without a trailing pressure relief surface 51.

Although not shown in the drawings, it will be understood that hydrodynamic thrust bearing surfaces may be located on the lower projection surface 26A of each impeller drive body to lift the impeller away from the bottom wall of the pumping chamber. Such lower hydrodynamic thrust bearings may be in addition to, or as an alternative to, the hydrodynamic thrust bearings located on the upper projection surfaces 26. The operational stiffness of the impeller will be influenced by the placement of hydrodynamic thrust bearing surfaces. For example, where lower hydrodynamic thrust bearings are used, the impeller may be initially positioned away from the upper motor stator. Where both upper and lower hydrodynamic thrust bearings are used, the geometry of the upper and lower hydrodynamic thrust bearing surfaces may differ to balance the resulting hydrodynamic thrust forces.

With further reference to FIG. 11, the hydrodynamic thrust bearing surface 47 is of approximately uniform width extending from the entrance region 48 to the exit region 49. In one embodiment, the entrance region has a rounded edge 54 contiguous with the substantially vertical sidewall of the shorter side 23A. In one embodiment, the edge 54 is relatively sharp, having a maximum radius of curvature of less than 0.010 inches, and may be as small as 0.005 inches or smaller. As indicated, each thrust bearing surface 47 is inclined upwardly from the entrance region 53 at an angle of less than 1 degree relative to the horizontal and terminates at approximately the flat bridging surface 52.

In one embodiment, each thrust bearing surface 47 is bounded along its length on opposite sides by inner and outer shrouds 57 and 58, respectively. In operation, the inner shroud 57 and the outer shroud 58 effectively minimize the leaking of blood fluid away from the thrust bearing surfaces thereby to assist maximizing the fluid layer thickness passing over the surface and minimizing fluid shear stress. The shrouds also serve to guide the blood toward the exit region 49 of the thrust bearing surface 47, from which it flows over the pressure relief surface 51 and into the next downstream fluid flow path 44. The top surface of the outer shroud 58 is relatively planar or flat and, in one embodiment, has a width of not less than 0.020 inches. The top surface of each of the shrouds 57 and 58 may be higher than the entrance region 53 of the bearing surface 47 by about 0.004 inches. At the exit region 49 of the bearing surface, the top surface of the shrouds 57 and 58 and the bearing surface may merge into the planar bridging surface 52.

With continuing reference to FIG. 11, in one embodiment, each juncture between the longer and shorter side walls and a support bar 42 between adjacent impeller bodies defines a concave channel extending completely around the juncture. These concave channels eliminate sharp transitions between the support bars and the impeller bodies that can result in undesirable thrombosis. Similarly, the outer and inner edges 55 and 55A, respectively, of the upper surface of each support bar are rounded to enhance blood flow and minimize thrombosis. In some embodiments, each of the inwardly facing surfaces 55B of each of the support bars 42 are inclined downwardly and outwardly toward the perimeter of the support bar to further enhance blood flow and minimize thrombosis.

Figure 13:
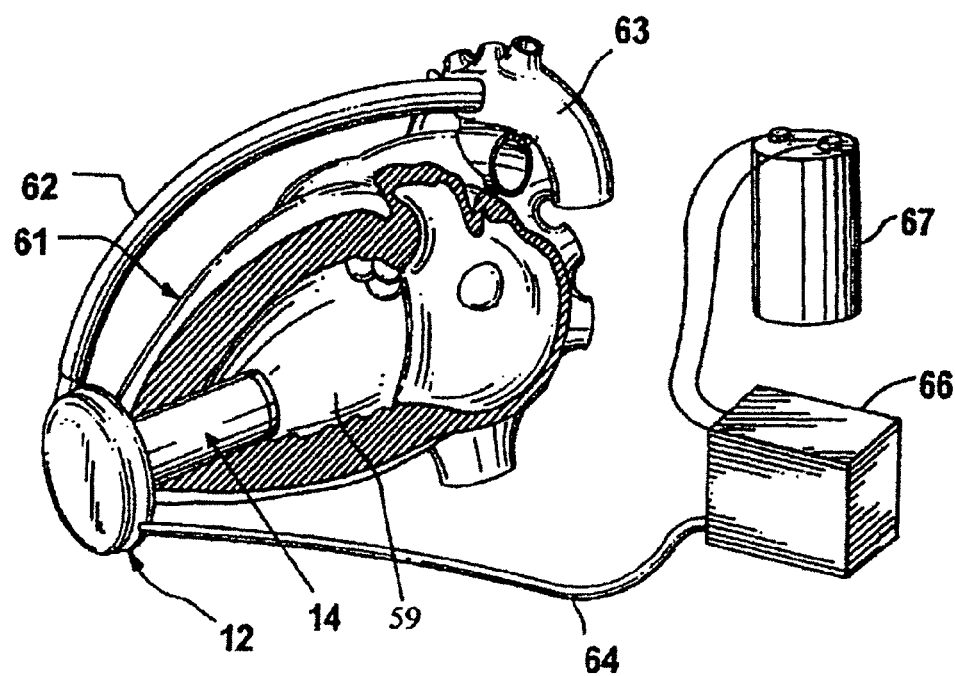
FIG. 13 is a system view of an implanted rotary blood pump according to an embodiment of the present invention.

With reference to FIG. 13, there is illustrated an implanted rotary blood pump according to an embodiment of the present disclosure. The cannula 14 is inserted apically into the left ventricle 59 of the patient's heart 61. A blood transport graft or tube 62 connects the blood outlet of the rotary blood pump to the patient's aorta 63. A power and control cable 64 may be connected to a controller 66 having a power source 67. The controller 66 and the power source 67 may be implanted within the patient's body or worn by the patient. The controller is used to provide clinicians information on how the device is performing, to provide run status and alarm conditions and controls the rotational speed of the impeller, as may be desired. For example, impeller rotational speed may be controlled by using a pulsed drive waveform and measuring the back emf of the rotor when the drive pulse is at zero. Such a technique is set forth in commonly owned International Publication No. WO 01/05023 A1, the disclosure of which is incorporated herein by reference.

In some embodiments, the cannula may be curved to facilitate the fit of the blood pump into the thoracic cavity of the patient or to improve blood flow characteristics. As seen in FIG. 14, a cannula 70 may have a single curve, such as an elbow-curve, or may have multiple curves to change the direction of the flow of the blood, as desired. The curvature of the cannula may be within the range of greater than 0° up to and including 180°, for example, 90° as illustrated in FIG. 14.

The cannula may be connected directly to the heart, for example, at the left ventricle. Alternatively, with reference to FIG. 15, an inflow tube 71 may be used to connect the cannula 14 to the heart. The inflow tube may be curved or bendable or permanently bent to facilitate the fit of the blood pump into the thoracic cavity of the patient and/or to improve blood flow characteristics. An attachable curved or bendable tube may be used with a straight cannula in place of or in addition to a curved cannula.

As an alternative to connecting the cannula directly to the left ventricle of the heart, the cannula, either directly or via an inflow tube, may be connected to the pulmonary artery. The pump may thereby be used to facilitate pumping of oxygenated blood from the lungs to the aorta. Pumps as disclosed herein may also be used to pump deoxygenated blood from the inferior vena cava to the right ventricle of the heart.

For connection to the heart, a ventricular connector may be used to facilitate the interface between the heart ventricle and the cannula. An example of such a ventricular connector can be found in U.S. patent application Ser. No. 10/799,534, filed Mar. 12, 2004, the disclosure of which is herein incorporated by reference. In this configuration, an O-ring seal is provided for insertion into a groove in a cylindrical ring attached to a sewing ring adapted to be sewn to the heart. The O-ring may be installed in the cylindrical ring so as to form a leak proof seal between the inflow cannula and the cylindrical ring.

The above-described embodiments of the present invention are illustrative and not restrictive. Various modifications or changes thereof may be made thereto without departing from the broader spirit and scope of the invention as set forth in the appended claims.

The invention claimed is:

1. A rotary blood pump comprising:
   a housing having a pumping chamber defined by a wall;
   at least one annular electromagnetic motor stator overlying an exterior surface of the wall;
   a rotatable impeller within the pumping chamber having a plurality of spaced apart impeller bodies, each impeller body having a pair of straight side walls of unequal length, the side walls of each impeller body extending from an inner edge to respective peripheral edges of each impeller body, the inner edge being forward of the peripheral edges in the direction of rotation of the impeller; and
   supports connecting the side walls of each impeller body to the side walls of adjacent impeller bodies proximal to the peripheral edges of each impeller body, the supports defining a ring having an outer circumference and an inner circumference, the side walls of each impeller body extending from the outer circumference and intersecting the inner circumference.

2. The rotary blood pump as claimed in claim 1, wherein the shorter of the side walls defines a leading surface of each impeller body.

3. The rotary blood pump as claimed in claim 1, wherein the impeller has a central opening defined by the inner edges of the impeller bodies.

4. The rotary blood pump of claim 2 in which none of the leading surfaces is perpendicular to any other leading surface.

5. The rotary blood pump of claim 2 in which none of the leading surfaces is perpendicular to any of the side walls of the impeller bodies.

6. The rotary blood pump of claim 1 in which blood flow passages are formed between adjacent impeller bodies, none of the blood flow passages being perpendicular to any other blood flow passage.

7. The rotary blood pump as claimed in claim 2, further comprising hydrodynamic thrust bearing surfaces on the impeller bodies extending from the leading surface and being adapted to constrain the axial position of the impeller relative to an interior surface of the wall of the pumping chamber when the impeller is rotating.

8. The rotary blood pump of claim 1, in which the motor stator is co-axial with the axis of rotation of the impeller.

9. The rotary blood pump of claim 8, in which the impeller has a circular circumference, the diameter of which is substantially the same as the diameter of the motor stator.

10. The rotary blood pump of claim 8, wherein the wall of the pumping chamber includes an upper wall and a lower wall remote from the upper wall, the impeller is disposed between interior surfaces of the upper and lower walls, and the motor stator includes a first motor stator overlying an exterior surface of the upper wall and a second motor stator overlying an exterior surface of the lower wall.

11. The rotary blood pump of claim 10 in which magnetic coupling between the impeller and magnetic forces provided by the motor stator constrain the radial position of the impeller when the impeller is rotating.

12. The rotary blood pump of claim 10, wherein the motor stator overlying the upper wall is closer to the impeller than the motor stator overlying the lower wall.

13. The rotary blood pump of claim 10 in which each of the motor stators is substantially annular in cross section and co-axial with the axis of rotation of the impeller.

14. The rotary blood pump of claim 13 in which the impeller has a circular circumference, the diameter of which is substantially the same as the diameter of each of the motor stators.

15. The rotary blood pump of claim 1, wherein the impeller includes a biocompatible magnetically isotropic material.

16. The rotary pump of claim 15, wherein the biocompatible magnetically isotropic material is a platinum-cobalt alloy.

17. The rotary blood pump of claim 1, wherein the impeller is coated with an organic polymer.

18. The rotary blood pump of claim 1 wherein the impeller bodies have interior cavities and permanent drive magnets sealed within the cavities.

19. The rotary blood pump of claim 1, wherein the impeller bodies have upper surfaces and lower surfaces separated from the upper surfaces by the side walls, the impeller bodies further including upper magnetic poles adjacent to the upper surfaces.

20. The rotary blood pump of claim 19, wherein the impeller bodies further include lower magnetic poles adjacent to the lower surfaces.

21. The rotary blood pump of claim 19, wherein magnetic coupling between the motor stator and the magnetic poles causes the impeller to rotate.

22. The rotary blood pump of claim 1 comprising from two to six of the impeller bodies.

23. The rotary blood pump of claim 7, further comprising substantially flat projection surfaces on the impeller bodies including inner and outer shrouds laterally adjacent to said hydrodynamic thrust bearing surfaces, and adapted to minimize fluid leakage away from said hydrodynamic thrust bearing surfaces.

24. The rotary blood pump of claim 7, wherein said rotary blood pump has no magnetic bearing having a permanent magnet at a fixed position with respect to said housing for exerting a constant polarity axially directed magnetic force.

25. The rotary blood pump of claim 8 comprising a cylindrical cannula aligned with the axis of rotation of said impeller, said motor stator being co-axial with said cylindrical cannula.

* * * * *